(12) United States Patent
Kanazawa et al.

(10) Patent No.: US 11,761,065 B2
(45) Date of Patent: Sep. 19, 2023

(54) TUNGSTEN WIRE AND TUNGSTEN PRODUCT

(71) Applicant: Panasonic Intellectual Property Management Co., Ltd., Osaka (JP)

(72) Inventors: Tomohiro Kanazawa, Osaka (JP); Naoki Kohyama, Osaka (JP); Yoshihiro Iguchi, Osaka (JP); Yui Nakai, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 136 days.

(21) Appl. No.: 17/604,859

(22) PCT Filed: Apr. 13, 2020

(86) PCT No.: PCT/JP2020/016278
§ 371 (c)(1),
(2) Date: Oct. 19, 2021

(87) PCT Pub. No.: WO2020/218058
PCT Pub. Date: Oct. 29, 2020

(65) Prior Publication Data
US 2022/0220591 A1 Jul. 14, 2022

(30) Foreign Application Priority Data
Apr. 26, 2019 (JP) .................. 2019-086166

(51) Int. Cl.
*C22C 27/04* (2006.01)
*A61L 31/02* (2006.01)
(Continued)

(52) U.S. Cl.
CPC ............ *C22C 27/04* (2013.01); *A61L 31/022* (2013.01); *A61L 31/14* (2013.01); *B21C 1/02* (2013.01);
(Continued)

(58) Field of Classification Search
None
See application file for complete search history.

(56) References Cited

U.S. PATENT DOCUMENTS

2018/0281231 A1\* 10/2018 Kanazawa ............. B23D 61/18

FOREIGN PATENT DOCUMENTS

| CN | 109591210 | | 4/2019 |
|---|---|---|---|
| CN | 109591210 A | \* | 4/2019 |
| JP | 6249319 | | 12/2017 |

OTHER PUBLICATIONS

Yih et al., "Tungsten: Sources, Metallurgy, Properties, and Applications", 1979, Plenum Press, pp. 207-222. (Year: 1979).\*
(Continued)

*Primary Examiner* — Xiaobei Wang
(74) *Attorney, Agent, or Firm* — GREENBLUM & BERNSTEIN, P.L.C.

(57) ABSTRACT

A tungsten wire is a tungsten wire containing tungsten or a tungsten alloy, a diameter of the tungsten wire is at most 100 μm, and a total number of torsional rotations to breakage per length of 50 mm of the tungsten wire is greater than or equal to $250 \times \exp(-0.026 \times D)$ when a tension that is 50% of a breakage tension of the tungsten wire is applied as a load, D denoting the diameter of the tungsten wire.

11 Claims, 8 Drawing Sheets

(51) Int. Cl.
*A61L 31/14* (2006.01)
*B21C 1/02* (2006.01)
*C22F 1/18* (2006.01)

(52) U.S. Cl.
CPC ......... *C22F 1/18* (2013.01); *Y10T 428/12431* (2015.01)

(56) References Cited

OTHER PUBLICATIONS

International Search Report issued in International Patent Application No. PCT/JP2020/016278, dated Jul. 14, 2020.
China Office Action issued in CN Application No. 202080028993.7, dated Mar. 8, 2022.
English Search Report issued in CN Application No. 202080028993.7 on Mar. 2, 2022.

\* cited by examiner

TUNGSTEN WIRE AND TUNGSTEN PRODUCT

TECHNICAL FIELD

The present invention relates to a tungsten wire and a tungsten product.

BACKGROUND ART

In recent years, tungsten wires that implement a high tensile strength have been under development (see Patent Literature (PTL) 1, for example).

CITATION LIST

Patent Literature

[PTL 1] Japanese Patent No. 6249319

SUMMARY OF INVENTION

Technical Problem

However, with the above-described conventional tungsten wire, there is a problem that the strength is not sufficient when torsion is applied.

In view of the above, the present invention provides a tungsten wire and a tungsten product that have a higher breakage strength against torsion than that of the conventional techniques.

Solution to Problem

In order to achieve the above-described object, a tungsten wire according to an aspect of the present invention is a tungsten wire containing tungsten or a tungsten alloy, a diameter of the tungsten wire is at most 100 µm, and a total number of torsional rotations to breakage per length of 50 mm of the tungsten wire is greater than or equal to $250 \times \exp(-0.026 \times D)$ when a tension that is 50% of a breakage tension of the tungsten wire is applied as a load, D denoting the diameter of the tungsten wire.

In addition, a tungsten product according to an aspect of the present invention includes the above-described tungsten wire.

Advantageous Effects of Invention

With the present invention, it is possible to provide a tungsten wire and a tungsten product that have a higher breakage strength against torsion than that of the conventional techniques.

DESCRIPTION OF EMBODIMENTS

The following describes in detail a tungsten wire and a tungsten product according to an embodiment of the present invention, with reference to the drawings. It should be noted that each of the embodiments described below shows a specific example of the present invention. The numerical values, shapes, materials, structural components, the disposition and connection of the structural components, a manufacturing process, an order of the manufacturing process, etc. described in the following embodiment are mere examples, and do not intend to limit the present disclosure, Among the structural components in the embodiments described below, those not recited in the independent claims will be described as optional structural components.

In addition, each diagram is a schematic diagram and not necessarily strictly illustrated. Accordingly, for example, scale sizes, etc. are not necessarily exactly represented. In each of the diagrams, substantially the same structural components are assigned with the same reference signs, and redundant descriptions will be omitted or simplified.

In addition, a term, such as "perpendicular" or "identical", representing a relationship between the components as well as a term, such as "circular", representing a form, and a numerical range are used in the present description. Such terms and range are each not representing only a strict meaning of the term or range, but implying that a substantially same range, e.g., a range that includes even a difference as small as few percentages, is connoted in the term or range.

Embodiment

Tungsten Wire

First, a configuration of a tungsten wire according to the present embodiment will be described.

Figure 1:
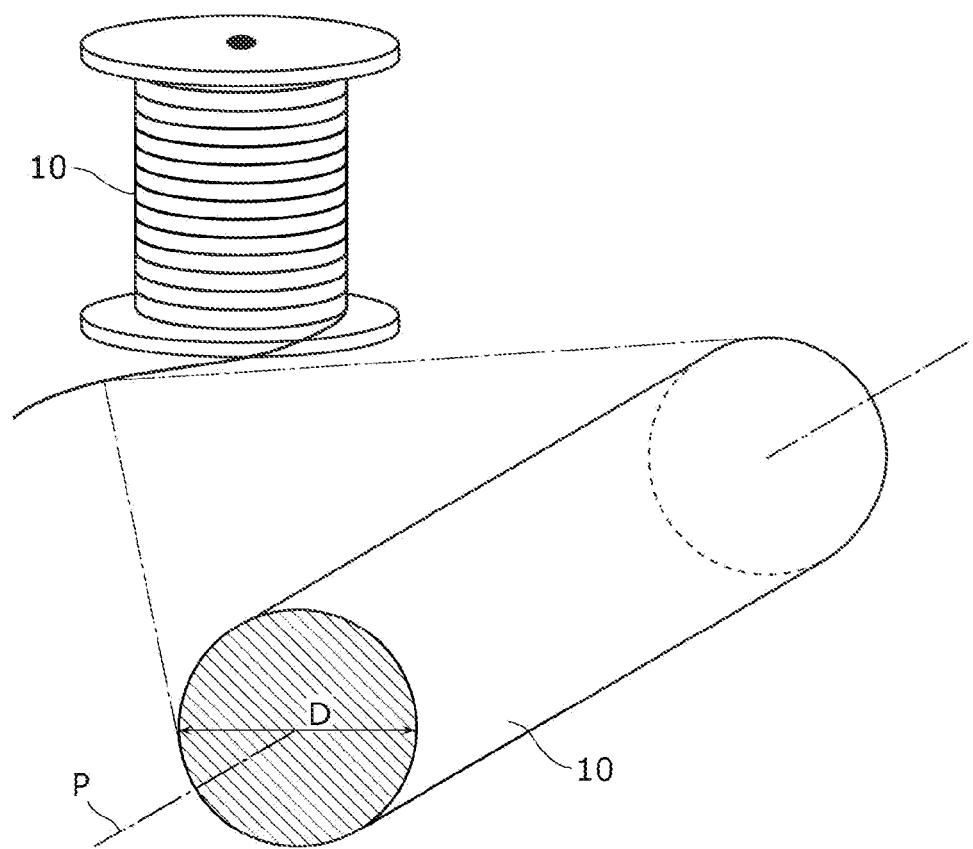
FIG. 1 is a perspective view schematically illustrating a tungsten wire according to an embodiment.

FIG. 1 is a perspective view schematically illustrating tungsten wire 10 according to the present embodiment. FIG. 1 illustrates an example in which tungsten wire 10 is wound around a winding core material. In addition, FIG. 1 schematically illustrates a partially enlarged view of tungsten wire 10.

Tungsten wire 10 contains one of tungsten (W) and a tungsten alloy. A tungsten content of tungsten wire 10 is, for example, at least 90 wt %. It should be noted that the tungsten content may be at least 95 wt %, or at least 99 wt %. Furthermore, the tungsten content may be at least 99.9 wt %, or at least 99.95 wt %. The tungsten content is the ratio of a weight of tungsten contained in tungsten wire 10 to a total weight of tungsten wire 10. The same holds true for the content of other metal elements such as rhenium (Re) and potassium (K) which will be described later. Tungsten wire 10 may contain inevitable impurities which are inevitably mixed therein through the processes of manufacturing.

The tungsten alloy is, for example, an alloy containing rhenium and tungsten (rhenium-tungsten alloy (ReW alloy)). It is possible to enhance the strength of tungsten wire 10 as the rhenium content increases. Meanwhile, an excessively high rhenium content degrades the workability of tungsten wire 10, making it difficult to render tungsten wire 10 thinner.

According to the present embodiment, the rhenium content of tungsten wire 10 is at least 0.1 wt % and at most 10 wt %. For example, the rhenium content may be at least 0.5 wt % and at most 5 wt %. One example of the rhenium content is 1 wt %, but the rhenium content may be 3 wt %.

Tungsten wire 10 has a diameter D that is less than or equal to 100 μm. The diameter D may be less than or equal to 80 μm, less than or equal to 60 μm, or less than or equal to 40 μm. The diameter D may be less than or equal to 30 μm, or less than or equal to 20 μm. The diameter D may be less than or equal to 10 μm The diameter D is, for example, greater than or equal to 5 μm.

According to the present embodiment, the diameter D of tungsten wire 10 is constant. However, the diameter of tungsten wire 10 need not necessarily be completely constant, and may differ at different portions along the axis by a certain percentage such as 1%. Tungsten wire 10 has, for example, a circular cross-section shape in the cross section perpendicular to axis P. It should be noted that the cross-section shape of tungsten wire 10 may be square, rectangle, oval, or the like.

Tungsten wire 10 has a tensile strength of at least 4800 MPa. The tensile strength of tungsten wire 10 may be at least 5000 MPa, or may be at least 5300 MPa. It is possible to implement tungsten wire 10 having a tensile strength higher than 5500 MPa, by adjusting the diameter D, the size of a crystalline grain of tungsten, etc. It should be noted that the tensile strength of tungsten wire 10 may be less than 4800 MPa.

In addition, an elastic modulus of tungsten wire 10 is at least 350 GPa and at most 450 GPa. Here, the elastic modulus is a longitudinal elastic modulus. An elastic modulus of piano wire is generally in a range of from 150 GPa to 250 GPa. In other words, tungsten wire 10 has an elastic modulus approximately twice as high as that of piano wire.

As having an elastic modulus higher than or equal to 350 GPa, tungsten wire 10 is resistant to deformation. Stated differently, tungsten wire 10 is less likely to elongate, Meanwhile, as having an elastic modulus lower than or equal to 450 GPa, it is possible to transform tungsten wire 10 when force of a certain strength is applied. Specifically, since tungsten wire 10 can be bent, when tungsten wire 10 is used as a saw wire, for example, it is possible to easily loop the saw wire over a guide roller or the like.

Tungsten wire 10 according to the present embodiment has a feature that the total number of torsional rotations to breakage is larger than that of the conventional techniques. The following describes the total number of torsional rotations to breakage.

Total Number of Torsional Rotations to Breakage

The total number of torsional rotations to breakage is a total number of torsional rotations necessary for tungsten wire 10 to break when torsion is applied to tungsten wire 10, The larger the total number of torsional rotations to breakage, the higher the strength of tungsten wire 10 against torsion.

The total number of torsional rotations to breakage is measured by conducting a torsion test. The torsion test is conducted using tungsten wire 10 that is cut out to a predetermined length L. More specifically, the axial ends of tungsten wire 10 which has length L are held, and a predetermined tension T is applied as a load to tungsten wire 10. One end of tungsten wire 10 is fixed, and the other end is rotated about the axis in a state in which the predetermined tension T is applied. The total number of rotations about the axis of the other end is the total number of torsional rotations N, The rotation of the other end of tungsten wire 10, i.e., torsion continues to be applied until tungsten wire 10 breaks. The total number of torsional rotations N at the time when tungsten wire 10 breaks is the total number of torsional rotations to breakage.

The inventors of the present application manufactured a plurality of samples of tungsten wire 10 (working example) based on a manufacturing method which will be described later, and measured a torsional breakage strength of each of the samples according to the working example, by conducting torsion tests. The inventors of the present application also manufactured samples according to a comparison example, and measured a torsional breakage strength of each of the samples according to the comparison example. The samples according to the comparison example are manufactured using a manufacturing method different from the manufacturing method of the samples according to the working example. The difference in the manufacturing method between the working example and the comparison example will be described later.

Length L of the samples for use in the torsion test is 50 mm. Tension T is a tension of 50% of a breakage tension of a tungsten wire. Here, the breakage tension of the tungsten wire is a tension at which tungsten wire 10 having length L is broken when a tension is applied to the tungsten wire without applying torsion. The breakage tension of the tungsten wire is, for example, at least 4N and at most 10N.

Each sample is a rhenium tungsten alloy wire. The rhenium content is 1 wt % and the tungsten content is 99 wt %.

Figure 2:
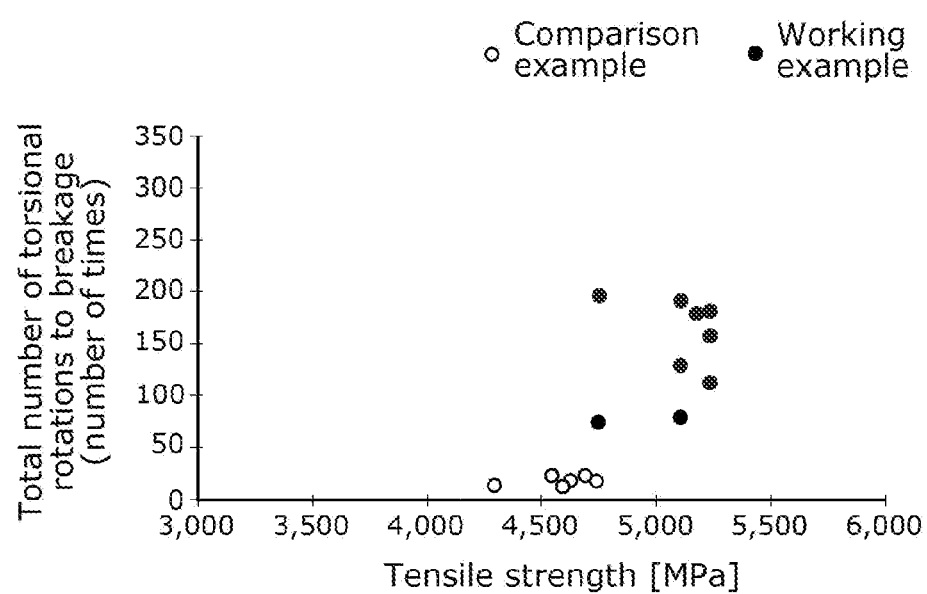
FIG. 2 is a diagram illustrating a measurement result showing the relationship between a tensile strength and a total number of torsional rotations to breakage of tungsten wires according to a working example and a comparison example.

FIG. 2 is a diagram illustrating a measurement result showing the relationship between a tensile strength and the total number of torsional rotations to breakage of tungsten wires according to the working example and the comparison example. In FIG. 2, the horizontal axis represents the tensile strength of tungsten wire 10, and the vertical axis represents the total number of torsional rotations to breakage of tungsten wire 10. In FIG. 2, the tensile strength of each of the samples is illustrated by plotting a black circle (working example) or a white circle (comparison example). The diameter D of each of the samples is 50 μm.

As illustrated in FIG. 2, the tensile strengths of the samples according to the working example were in a range of from at least approximately 4700 MPa to at most approximately 5300 MPa. The tensile strengths of the samples according to the comparison example were at least approximately 4300 MPa and less than approximately 4800 MPa.

As illustrated in FIG. 2, with the samples according to the comparison example, the total number of torsional rotations to breakage was less than 30 times, irrespective of the tensile strength. On the other hand, with the samples according to the working example, the total number of torsional rotations to breakage was at least 70 times. A sample with which the total number of torsional rotations to breakage amounted to 200 times was also obtained. In any of the samples, from the sample having a tensile strength of approximately 4750 MPa to the sample having a tensile strength of approximately 5200 MPa, the total number of torsional rotations to breakage more than twice that of the samples according to the comparison example was realized.

In addition, the inventors of the present invention manufactured samples having different diameters D according to each of the working example and the comparison example. For example, when the diameter D is 30 μm, the tensile strength of the samples according to the working example was in a range of from at least approximately 4800 MPa to at most approximately 5800 MPa. For example, the tensile strength of the sample according to the comparison example when a diameter D is 30 μm was in a range of from at least approximately 3700 MPa to at most approximately 4800 MPa.

In addition, the inventors of the present invention measured the relationship between the diameter D and the total number of torsional rotations to breakage. The measurement result is indicated in FIG. 3.

Figure 3:
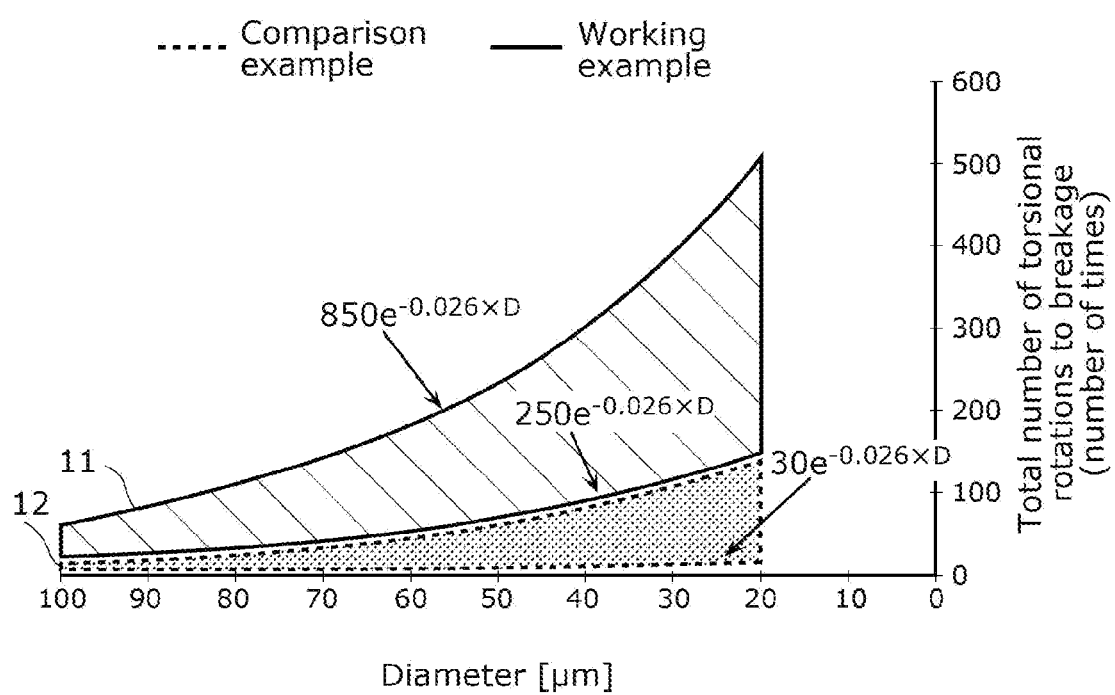
FIG. 3 is a diagram illustrating a measurement result showing the relationship between a diameter and the total number of torsional rotations to breakage of the tungsten wires according to the working example and the comparison example.

FIG. 3 is a diagram illustrating measurement results showing the relationship between a diameter D and a total number of torsional rotations to breakage of tungsten wires 10 according to the working example and the comparison example. In FIG. 3, the horizontal axis represents a diameter D of tungsten wire 10, and the vertical axis represents a total number of torsional rotations to breakage of tungsten wire 10.

When the diameter is in the range of from at least 20 μm and at most 100 μm, the total number of torsional rotations to breakage of each of the samples according to the working example was included in region 11 which is enclosed by a solid line and shaded by hatched lines in FIG. 3. More specifically, the total number of torsional rotations to breakage of the sample according to the working example is greater than or equal to $250 \times \exp(-0.026 \times D)$, In other words, the curve representing the lower limit of the total number of torsional rotations to breakage of the sample is expressed as $250 \times \exp(-0.026 \times D)$ with a diameter D as the variable. In addition, the total number of torsional rotations to breakage of the sample according to the working example is less than or equal to $850 \times \exp(-0.026 \times D)$. In other words, the curve representing the upper limit of the total number of torsional rotations to breakage of the sample is expressed as $850 \times \exp(-0.026 \times D)$ with a diameter D as the variable. These curves representing the upper limit and the lower limit were calculated by fitting based on the result of actual measurements of the total number of torsional rotations to breakage (specifically, the upper limit and the lower limit for each diameter D).

Meanwhile, the total number of torsional rotations to breakage of the sample according to the comparison example was included in region 12 which is enclosed by the dashed line and shaded by dots in FIG. 3. More specifically, the total number of torsional rotations to breakage of the sample according to the comparison example was greater than or equal to $30 \times \exp(-0.026 \times D)$ times and less than $250 \times \exp(-0.026 \times D)$ times.

As described above, the sample according to the working example has a thin diameter D of 100 μm or less and a tensile strength of 4800 MPa or more, and it has been implemented that the total number of torsional rotations to breakage per length of 50 mm is greater than or equal to $250 \times \exp(-0.026 \times D)$ times when tension T that is 50% of the breakage tension of tungsten wire 10 is applied as a load. In other words, with tungsten wire 10 according to the present embodiment, it is possible to implement excellent properties of not only being thin and high in tensile strength, but also being extremely high in breakage strength against torsion.

It should be noted that, in the case where the tungsten content or the rhenium content contained in tungsten wire 10 is different, it is also possible to increase the breakage strength against torsion in addition to implementing excellent properties of being thin and high in tensile strength.

Manufacturing Method of Tungsten Wire

Next, a manufacturing method of tungsten wire 10 according to the present embodiment will be described with reference to FIG. 4, and FIG. 5.

Figure 4:
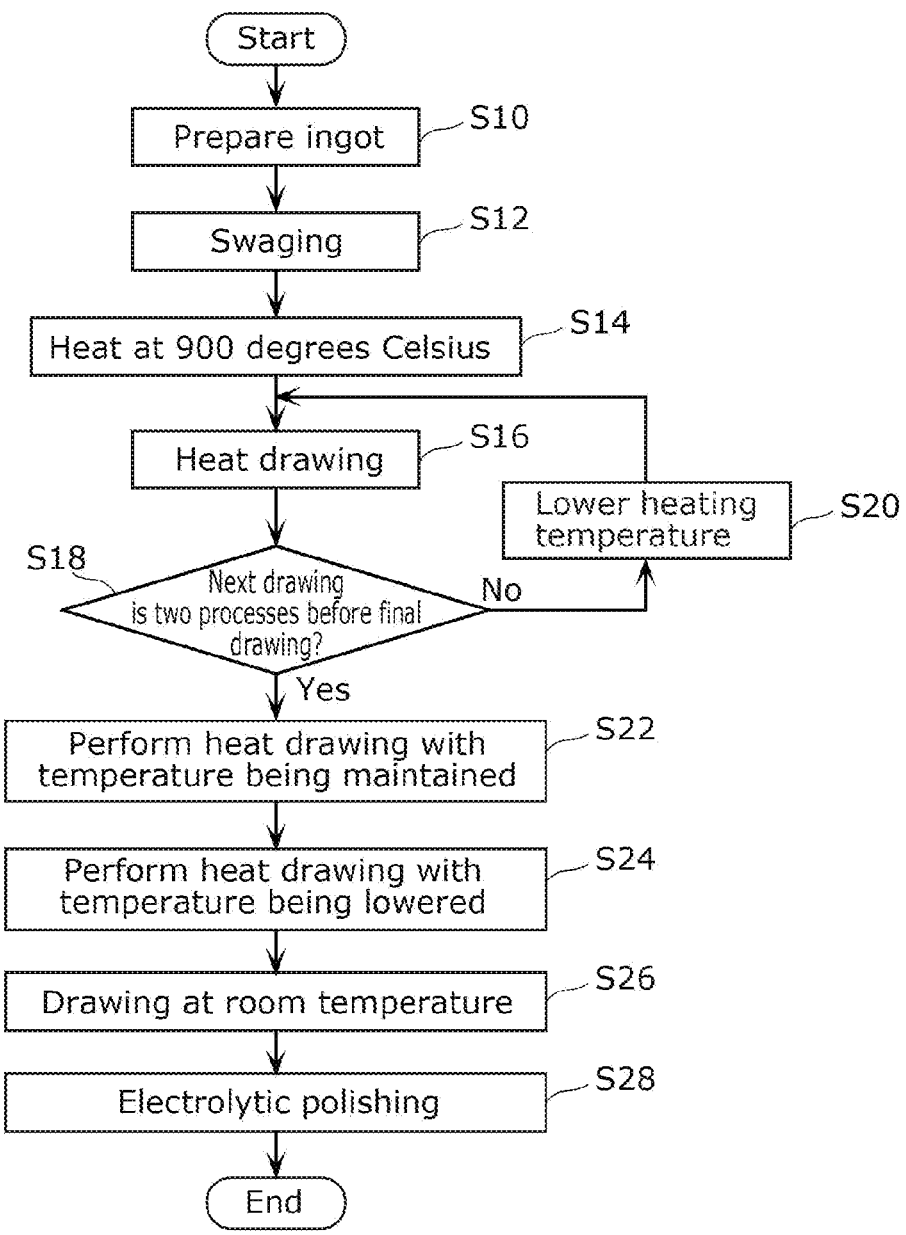
FIG. 4 is a flowchart illustrating a manufacturing method of the tungsten wire according to the embodiment.

FIG. 4 is a flowchart illustrating the manufacturing method of tungsten wire 10 according to the present embodiment. FIG. 5 is a diagram illustrating a heating temperature in a drawing process included in the manufacturing method of tungsten wire 10 according to the present embodiment. It should be noted that FIG. 5 illustrates the case where the drawing is performed n times. For example, n is a natural number greater than or equal to 5.

As illustrated in FIG. 4, first, a tungsten ingot is prepared (S10). More specifically, a tungsten ingot is manufactured by preparing an aggregation of tungsten powders and pressing and sintering the prepared aggregation of tungsten powders.

It should be noted that, when tungsten wire 10 containing a tungsten alloy is manufactured, a mixture resulting from mixing tungsten powders and metal powders (rhenium powders, for example) at a predetermined proportion is prepared instead of the aggregation of tungsten powders. An average grain diameter of a tungsten powder and a rhenium powder is in a range of from at least 3 μm to at most 4 μm, for example, but not limited to this example. The mixing ratio of the tungsten powder and the rhenium powder depends on the content ratio of tungsten and rhenium in tungsten wire 10 to be manufactured. The specific gravity of the manufactured tungsten ingot is, for example, at least 17.4 g/cm$^3$, but it may be at least 17.8 g/cm$^3$ and at most 18.2 g/cm$^3$.

Next, swaging processing is applied to the manufactured tungsten ingot (S12). More specifically, the tungsten ingot is press-forged from its periphery and extended to be a tungsten wire having a wire shape. It should be noted that the tungsten ingot may be subjected to rolling processing instead of the swaging processing.

For example, a tungsten ingot having a diameter of approximately at least 15 mm and approximately at most 25 mm is shaped into a tungsten wire having a diameter of approximately 3 mm, by repeatedly applying the swaging processing to the tungsten ingot. Annealing is performed during the swaging processing to ensure workability in the subsequent processes. For example, annealing at 2400 degrees Celsius is performed in a diameter range of from at least 8 mm to at most 10 mm. However, in order to enhance a tensile strength by crystal grain refinement, annealing is not performed in the swaging processing with a diameter of less than 8 mm.

Next, prior to heat drawing, the tungsten wire is heated at 900 degrees Celsius (S14). More specifically, the tungsten wire is heated directly by a burner or the like. An oxide layer is formed on the surface of the tungsten wire by heating the tungsten wire, to prevent wire breakage during the processing in the subsequent heat drawing.

Next, heat drawing is carried out (S16). More specifically, drawing of the tungsten wire, namely, a wire drawing process (thinning) of the tungsten wire, is performed using a single wire drawing die, while heating is performed. The heating temperature T1 of the first drawing (see FIG. 5) is, for example, 1000 degrees Celsius. The workability of a tungsten wire is enhanced as the heating temperature increases, and thus it is possible to easily perform the drawing. The reduction in area of the tungsten wire by one drawing using a single wire drawing die is, for example, at least 10% and at most 40%. In the drawing processing, a lubricant including graphite dispersed in water may be used.

After the drawing processing, electrolytic polishing may be performed to smooth the surface of the tungsten wire. The electrolytic polishing is carried out, for example, as a result of generation of a potential difference between a tungsten wire and a counter electrode in a state in which the tungsten wire and counter electrode are bathed into electrolyte, e.g., aqueous sodium hydroxide.

The heat drawing (S16) is repeatedly performed until a tungsten wire having a desired diameter is obtained (No in S18). Here, a desired diameter is a diameter at the stage two steps before the final drawing process (S26), and is at least 170 μm and at most 250 μm for example, but not limited to this example.

In the repeating of heat drawing, a wire drawing die having a smaller pore diameter than a pore diameter of a wire drawing die used in the immediately-before drawing is used. In addition, when the heat drawing is repeated, the heating temperature is lowered as illustrated in FIG. 4 (S20), In other words, the tungsten wire is heated at a heating temperature lower than a heating temperature applied in the immediately-before drawing. For example, as illustrated in FIG. 5, the heating temperature T2 in the n−3th drawing process is lower than a heating temperature in the n−4th drawing process performed immediately before. In addition, the heating temperature T2 in the n−3th drawing process is lower than any of the heating temperatures in the previous drawing processes. In this manner, as the diameter decreases, the heating temperature in the drawing process is gradually reduced.

When a tungsten wire of the desired diameter is obtained and the next drawing process is two processes before the final drawing process (i.e., the n−2th drawing) (Yes in S18), the heat drawing is performed with the temperature being maintained (S22). More specifically, as illustrated in FIG. 5, the heating temperature of the n−2th drawing process is the same as the heating temperature of the n−3th drawing process. Temperature T2 is higher than the primary recrystallization temperature of tungsten, Temperature T2 is in the range of from at least 900 degrees Celsius to at most 1000 degrees Celsius, for example.

It is possible to facilitate the primary recrystallization of tungsten contained in the tungsten wire, by increasing the temperature in the drawing two steps before the final drawing process. With this, a void in the tungsten wire is reduced, and extension of the crystal grains in the axial direction is facilitated. It is considered that this allows an increase in the total number of torsional rotations to breakage.

Figure 5:
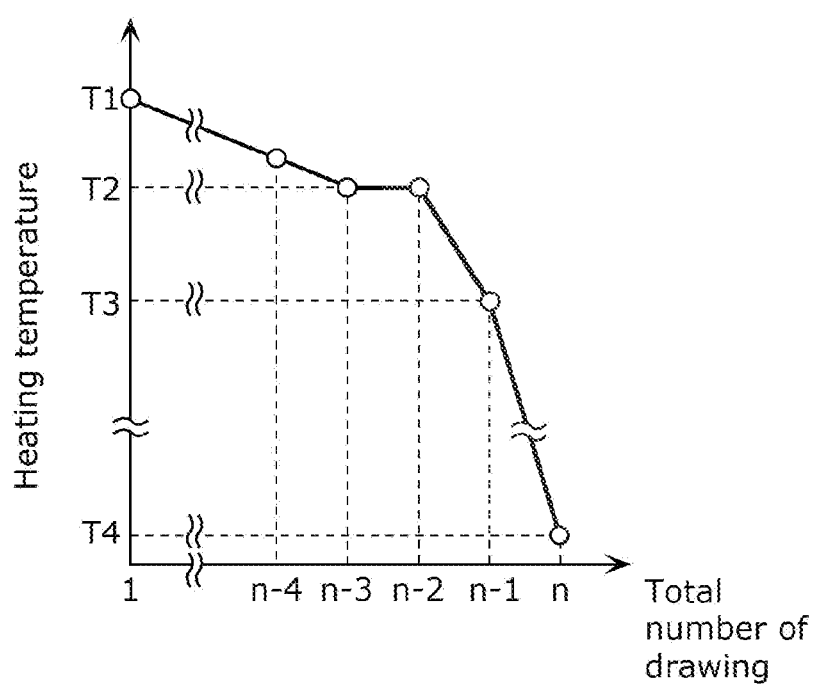
FIG. 5 is a diagram illustrating a heating temperature in a drawing process included in a manufacturing method of the tungsten wire according to the embodiment.

Next, one step before the final drawing process, the heat drawing is performed with the temperature being lowered (S24), As illustrated in FIG. 5, the heating temperature T3 of the n−1th drawing process is lower than the heating temperature T2 of n−3th drawing process. Temperature T3 is lower than the recrystallization temperature of tungsten. Temperature T3 is in the range of from at least 600 degrees Celsius to at most 700 degrees Celsius, for example. Heat drawing is performed at a low temperature so as to contribute to refinement of crystal grains. At this time, it is necessary to lower the heating temperature of the die. For example, the heating temperature of the die is in a range of from at least 300 degrees Celsius to at most 350 degrees Celsius, but is not limited to this range.

It should be noted that the heating temperature in the first to n−3th heating drawing is adjusted according to the amount of oxides attached to the surface of the tungsten wire, More specifically, the heating temperature is adjusted such that the amount of oxide is in the range of from at least 0.8 wt % to at most 1.6 wt % of the tungsten wire, thereby ensuring the drawing workability of the n−2th and n−1th heating drawing. In the repeating of heat drawing, electrolytic polishing may be omitted.

Next, the final drawing is performed at room temperature (S26). More specifically, a tungsten wire is drawn without heating, thereby achieving further refinement of crystal grains. In addition, the drawing at room temperature yields an advantageous effect of aligning crystal orientations in a processing axis direction (specifically, a direction parallel to axis P). The room temperature is, for example, a temperature in a range of from at least 0 degrees Celsius to at most 50 degrees Celsius, and is 30 degrees Celsius as one example.

In the drawing at room temperature, the tungsten wire is drawn using a plurality of wire drawing dies having different pore diameters. In the drawing at room temperature, a liquid lubricant such as a water-soluble lubricant is used. Since heating is not carried out in the drawing at room temperature, liquid evaporation is inhibited. Accordingly, a sufficient function as a lubricant can be exerted.

In contrast to the heat drawing at 600 degrees Celsius or higher which is the traditional tungsten wire processing method conventionally performed, the tungsten wire is not heated and is processed while being cooled with the liquid lubricant. As a result, it is possible to inhibit dynamic recovery and dynamic recrystallization, contribute to the refinement of crystal grains without wire breakage, and achieve a high tensile strength. In addition, along with crystal grain refinement, elongation of the crystals in the axial direction is implemented, thereby contributing to a significant increase in torsional strength.

Lastly, electrolytic polishing is performed on the tungsten wire having a diameter D resulting from the drawing at room temperature (S28). The electrolytic polishing is carried out, for example, as a result of generation of a potential difference between a tungsten wire and a counter electrode in a state in which the tungsten wire and counter electrode are bathed into electrolyte, e.g., aqueous sodium hydroxide.

Through the above-described processes, tungsten wire 10 according to the present embodiment is manufactured. Through the above-described manufacturing processes, tungsten wire 10 immediately after manufacturing has a length of, for example, at least 50 km, and thus is industrially available. Tungsten wire 10 is cut to a suitable length according to the aspect in which tungsten wire 10 is to be used, and can also be used in a shape of a needle or a stick. As described above, tungsten wire 10 according to the present embodiment can be mass-produced industrially and used for various tungsten products.

It should be noted that the tungsten wires according to the comparison example illustrated in FIG. 2 and FIG. 3 are manufactured by hot drawing, as it is called. For example, in the first drawing process, the wire is heated at a temperature of at least 1050 degrees Celsius and at most 1150 degrees Celsius. As the diameter decreases, the heating temperature is lowered and the drawing is repeatedly performed. In the final drawing process, the wire is heated at a temperature of at least 700 degrees Celsius and at most 800 degrees Celsius.

As described above, the Comparison example and the working example differ mainly in the heating temperature in the drawing process. It is possible to increase the total number of torsional rotations to breakage of the samples according to the working example to be larger than the total number of torsional rotations to breakage of the samples according to the comparison example, by performing the drawing at room temperature in the final drawing process, as explained with reference to FIG. 2 and FIG. 3. Furthermore, by making the heating temperature in the drawing process two steps before the final drawing process substantially the same as the heating temperature in the drawing process performed immediately before, it is possible to further increase the total number of torsional rotations to breakage of the samples according to the working example. In addition, by setting the heating temperature of the die so as to fall within the range of from at least 300 degrees Celsius and at most 350 degrees Celsius in the drawing process one step before the final wire drawing process, it is possible to further increase the total number of torsional rotations to breakage of the samples according to the working example.

Each of the processes indicated in the manufacturing method of tungsten wire 10 is carried out, for example, as an in-line process. More specifically, the plurality of wire drawing dies used in Steps S16, S22, and S24 are arranged in descending order of pore diameters in a production line. A heating device such as a burner is disposed between the respective wire drawing dies. In addition, an electrolytic polishing device may be disposed between the respective wire drawing dies. The plurality of wire drawing dies used in Step S26 are arranged in descending order of pore diameters on the downstream side (i.e., the subsequent-process side) of the wire drawing dies used in Steps S16, S22, and S24, and the electrolytic polishing device is disposed on the downstream side of the wire drawing die having the smallest pore diameter. It should be noted that each of the processes may be individually performed.

Tungsten Product

The following describes a specific example of a tungsten product which includes tungsten wire 10 according to the present embodiment.

(Saw Wire)

Figure 6:
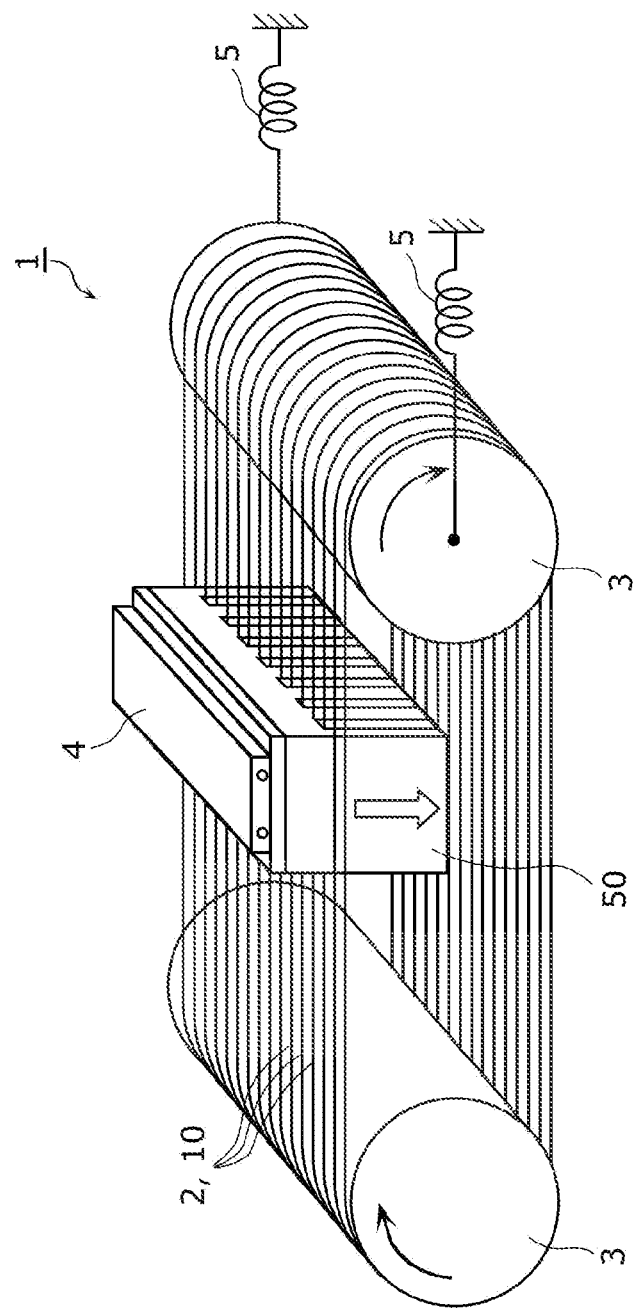
FIG. 6 is a perspective view illustrating a cutting apparatus including a saw wire that is an example of a tungsten product according to the embodiment.

Tungsten wire 10 according to the present embodiment can be used, for example, as saw wire 2 of cutting apparatus 1 that cuts an object such as a silicon ingot or concrete as illustrated in FIG. 6. FIG. 6 is a perspective view illustrating cutting apparatus 1 including saw wire 2 that is an example of a tungsten product according to the present embodiment.

As illustrated in FIG. 6, cutting apparatus 1 is a multi-wire saw including saw wire 2. Cutting apparatus 1 produces wafers by, for example, cutting ingot 50 into thin slices. Ingot 50 is, for instance, a silicon ingot including single-crystal silicon. More specifically, cutting apparatus 1 simultaneously produces a plurality of silicon wafers by slicing ingot 50 using a plurality of saw wires 2.

It should be noted that ingot 50 is a silicon ingot but is not limited to such. For example, an ingot including other substance such as silicon carbide or sapphire may be employed. Alternatively, an object to be cut by cutting apparatus 1 may be concrete, glass, etc.

According to the present embodiment, saw wire 2 includes tungsten wire 10. More specifically, saw wire 2 is quite simply tungsten wire 10 according to the present embodiment. Alternatively, saw wire 2 may include tungsten wire 10 and a plurality of abrasive particles included in a surface of tungsten wire 10.

As illustrated in FIG. 6, cutting apparatus 1 further includes two guide rollers 3, ingot holder 4, and tension releasing device 5.

A single saw wire 2 is looped multiple times over and across two guide rollers 3. Here, for convenience of explanation, one loop of saw wire 2 is regarded as one saw wire 2, and it is assumed that a plurality of saw wires 2 are looped over and across two guide rollers 3. Stated differently, in the description below, the plurality of saw wires 2 form a single continuous saw wire 2, It should be noted that the plurality of saw wires 2 may be a plurality of saw wires that are separated from one another.

Each of the two guide rollers 3 rotates in a state in which the plurality of saw wires 2 are straightly tightened with a predetermined tension, and thereby causes the plurality of saw wires 2 to rotate at a predetermined speed. The plurality of saw wires 2 are disposed in parallel to one another and are equally spaced. More specifically, each of the two guide rollers 3 is provided with grooves positioned at predetermined intervals for saw wires 2 to fit in. The intervals between the grooves are determined according to the thickness of the wafers desired to be sliced off. The width of the groove is substantially the same as the diameter of saw wire 2.

It should be noted that cutting apparatus 1 may include three or more guide rollers 3. Saw wires 2 may be looped over and across the three or more guide rollers 3.

Ingot holder 4 holds ingot 50 which is an object to be cut, Ingot holder 4 pushes ingot 50 through saw wires 2, and thereby ingot 50 is sliced by saw wares 2.

Tension releasing device 5 is a device that releases tension exerted on saw wire 2. Tension releasing device 5 is, for example, an elastic body such as a coiled or plate spring. As illustrated in FIG. 6, tension releasing device 5 that is a coiled spring, for example, has one end connected to guide roller 3 and the other end fixed to a predetermined wall surface. Tension releasing device 5 is capable of releasing the tension exerted on saw wire 2, by adjusting the position of guide roller 3.

It should be noted that, although not illustrated in the diagram, cutting apparatus 1 may be a cutting apparatus of a free abrasive particle type, and may include a feeder that feeds slurry to saw wires 2. The slurry is a cutting fluid such as a coolant including abrasive particles dispersed therein. The abrasive particles included in the slurry are fixed to saw wire 2, and thereby it is possible to easily cut ingot 50.

Saw wire 2 including tungsten wire 10 having a high tensile strength can be looped over and across guide rollers 3 with a strong tension. Accordingly, vibrations of saw wire 2 caused during the process of cutting ingot 50 are inhibited, and thus it is possible to reduce the kerf loss of ingot 50. In addition, since tungsten wire 10 has a high breakage strength against torsion, saw wire 2 is resistant to breakage even when saw wire 2 is twisted during use, and thus it is possible to increase the reliability of cutting apparatus 1.

(Twisted Wire and Rope)

Figure 7:
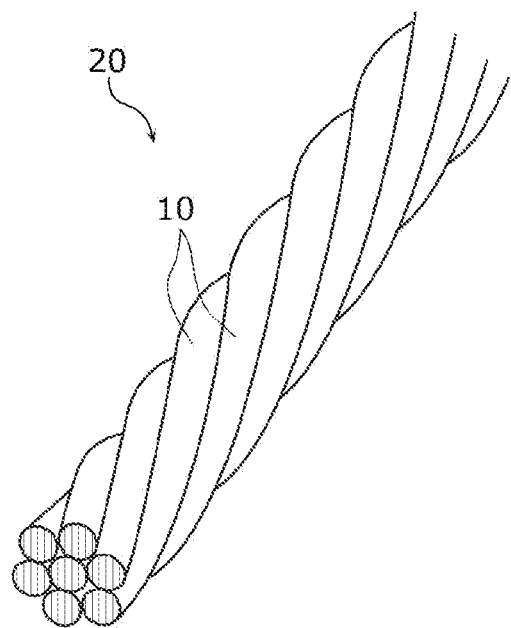
FIG. 7 is a perspective view illustrating a portion of a twisted wire that is an example of the tungsten product according to the embodiment.

Tungsten wire 10 according to the present embodiment can be used as twisted wire 20 as illustrated in FIG. 7. FIG. 7 is a perspective view illustrating a portion of twisted wire 20 that is an example of the tungsten product according to the present embodiment.

As illustrated in FIG. 7, twisted wire 20 includes a plurality of tungsten wires 10. Twisted wire 20 is manufactured by twisting the plurality of tungsten wires 10 together as strands.

Twisted wire 20 is a piled yarn obtained by performing twisting processing on the plurality of tungsten wires 10, for example. Alternatively, twisted wire 20 is a covered yarn obtained by performing covering processing on the plurality of tungsten wires 10. It should be noted that it is not necessary that all of the plurality of strands included in twisted wire 20 are tungsten wires 10. For example, twisted wire 20 may be configured by twisting tungsten wire 10 and a carbon steel wire together.

Figure 8:
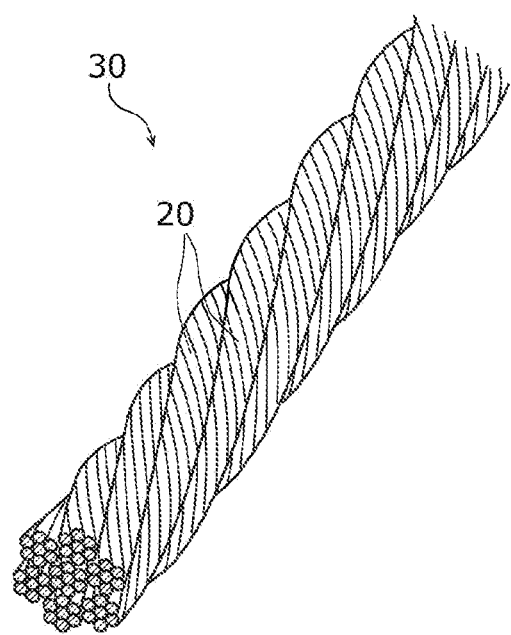
FIG. 8 is a perspective view illustrating a portion of a rope that is an example of the tungsten product according to the embodiment.

In addition, as illustrated in FIG. 8, rope 30 may also be manufactured by further twisting twisted wires 20 together. FIG. 8 is a perspective view illustrating a portion of rope 30 that is an example of the tungsten product according to the present embodiment.

As illustrated in FIG. 8, rope 30 is manufactured by twisting a plurality of twisted wires 20 together as small ropes (strands). It is possible to increase the strength of rope 30 by making a twisting direction (e.g., S-twist) of rope 30 different from a twisting direction of twisted wire 20 (e.g., Z-twist).

Since tungsten wire 10 has a high breakage strength against torsion, twisted wire 20 and rope 30 manufactured by performing twisting processing on tungsten wire 10 are resistant to breakage. As a result, highly reliable twisted wire 20 and rope 30 can be realized.

It should be noted that a total number of tungsten wires 10 and a total number of twists used for twisting each of twisted wires 20 and ropes 30 are not particularly limited.

(Catheter)

Figure 9:
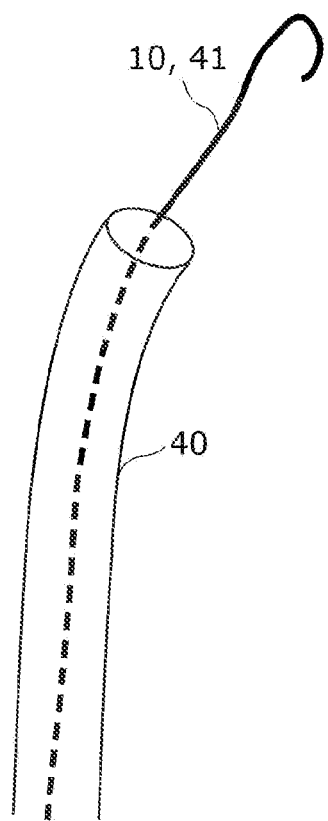
FIG. 9 is a perspective view illustrating a portion of a catheter that is an example of the tungsten product according to the embodiment.

Tungsten wire 10 according to the present embodiment can be used also as medical device components. FIG. 9 is a perspective view illustrating a portion of catheter 40 that is an example of the tungsten product according to the present embodiment.

Catheter 40 is an example of the medical device component. As illustrated in FIG. 9, catheter 40 is an elastic component having a tubular shape. Guide wire 41 is inserted inside catheter 40. Guide wire 41 is tungsten wire 10. In other words, it is possible to use tungsten wire 10 according to the present embodiment as guide wire 41 of catheter 40. Alternatively, tungsten wire 10 can be used also as a reinforcement wire for the catheter.

(Others)

Tungsten wire 10 can be used also as a metal mesh such as a screen mesh for screen printing. For example, such a screen mesh includes a plurality of tungsten wires 10 woven as warp and weft yarns.

In addition, tungsten wire 10 can be used also as a medical needle or an inspection probe needle which are examples of the medical device component. Furthermore, tungsten wire 10 can be used also as, for example, a reinforcement wire for an elastic component such as a tire, a conveyer belt, or the like. For example, a tire includes a plurality of tungsten wires 10 bundled in layers as a belt or carcass ply.

Advantageous Effect, Etc.

As described above, tungsten wire 10 according to the present embodiment is a tungsten wire containing tungsten or a tungsten alloy, a diameter D of tungsten wire 10 is at most 100 μm, and a total number of torsional rotations to breakage per length of 50 mm of tungsten wire 10 is greater than or equal to 250×exp(−0.026×D) when a tension that is 50% of a breakage tension of tungsten wire 10 is applied as a load, D denoting the diameter of tungsten wire 10.

According to this configuration, tungsten wire 10 that has a higher breakage strength against torsion than conventional techniques, and is sufficiently thin can be implemented.

In addition, for example, a tensile strength of tungsten wire 10 is at least 4800 MPa.

According to this configuration, tungsten wire 10 that has both a high breakage strength against torsion and a high tensile strength, and is sufficiently thin can be implemented.

In addition, for example, a tungsten content of tungsten wire 10 is at least 90 wt %.

According to this configuration, even in the case where tungsten wire 10 contains a tungsten alloy, it is possible to set the rhenium content to be less than 10 wt %, for example. As a result, it is possible to enhance the workability of tungsten wire 10.

In addition, for example, a tungsten product according to the present embodiment includes tungsten wire 10. In addition, for example, the tungsten product is a medical device component such as saw wire 2, twisted wire 20, rope 30, catheter 40, or the like.

According to this configuration, a tungsten product is manufactured by using tungsten wire 10 that has a higher breakage strength against torsion than conventional techniques, and is sufficiently thin. As a result, it is possible to inhibit wire breakage or the like during use of the tungsten product. For that reason, it is possible to implement a highly reliable tungsten product.

Others

Although the tungsten wire and tungsten product according to the present invention have been described thus far, based on the above-described embodiment, the present invention is not limited to the above-described embodiment.

For example, the metal contained in the tungsten alloy need not be rhenium. The tungsten alloy may be an alloy of tungsten and metal of at least one type different from tungsten. The metal different from tungsten is, for example, a transition metal, such as iridium (Ir), ruthenium (Ru), or osmium (Os). The content of the metal different from tungsten is, for example, at least 0.1 wt % and at most 10 wt %, but is not limited to this example. For example, the content of the metal different from tungsten &so may be less than 0.1 wt % or may be greater than 10 wt %, The same holds true for rhenium.

In addition, for example, the tensile strength of tungsten wire 10 may be less than 4800 MPa.

In addition, for example, tungsten wire 10 may contain tungsten doped with potassium (K). Potassium in tungsten wire 10 is present in the grain boundaries of tungsten. A tungsten content of tungsten wire 10 is, for example, at least 99 wt %.

A potassium content of tungsten wire 10 is at most 0.01 wt %, but is not limited to this example. For example, the potassium content of tungsten wire 10 may be at least 0.003 wt % and at most 0.010 wt %. As one example, the potassium content of tungsten wire 10 is 0.005 wt %.

Since the tungsten wire contains a subtle amount of potassium, crystal grain growth in the radial direction of the tungsten wire is inhibited. In other words, since the width of the surface crystal grains can be reduced, it is possible to increase the tensile strength.

The diameter, elastic modulus, tensile strength, and total number of torsional rotations to breakage of the tungsten wire containing potassium-doped tungsten (Le, potassium-doped tungsten wire) are equivalent to those of the above-described embodiment.

The potassium-doped tungsten wire can be manufactured through a manufacturing method equivalent to the manufacturing method of the embodiment, by using a doped tungsten powder doped with potassium instead of a tungsten powder.

In addition, for example, the surface of tungsten wire 10 may be coated by an oxide film, a nitride film, or the like.

Additionally, embodiments arrived at by those skilled in the art making modifications to the above embodiment, as well as embodiments arrived at by combining various structural components and functions described in the above embodiment without materially departing from the novel teachings and advantages of the present invention are intended to be included within the scope of the present invention.

The invention claimed is:

1. A tungsten wire containing tungsten or a tungsten alloy, wherein
    a diameter of the tungsten wire is at most 100 μm, and
    in a state that a tension that is 50% of a breakage tension of the tungsten wire is applied to the tungsten wire as a load, a total number of torsional rotations to breakage per length of 50 mm of the tungsten wire is greater than or equal to 250×exp(−0.026×D), where D denotes the diameter of the tungsten wire.

2. The tungsten wire according to claim 1, wherein
    a tensile strength of the tungsten wire is at least 4800 MPa.

3. The tungsten wire according to claim 1, wherein
    a tungsten content of the tungsten wire is at least 90 wt %.

4. A tungsten product comprising: the tungsten wire according to claim 1.

5. The tungsten product according to claim 4, wherein
    the tungsten product is a saw wire, a twisted wire, a rope, or a medical device component.

6. A tungsten wire containing tungsten or a tungsten alloy, wherein
    a diameter of the tungsten wire is at most 100 μm, and
    in a state that a tension that is 50% of a breakage tension of the tungsten wire is applied to the tungsten wire as a load, a total number of torsional rotations to breakage per length of 50 mm of the tungsten wire is greater than or equal to 250×exp(−0.026×D), where D denotes the diameter of the tungsten wire,
    wherein the tungsten wire is formed by a wire drawing process,
    wherein, in the wire drawing process, the tungsten wire is subjected to an elevated-heat drawing,
    wherein the elevated-heat heat drawing is two drawings before a final drawing in the wire drawing process and is performed at a temperature equal to a temperature of a preceding heat drawing that precedes the elevated-heat drawing in the wire drawing process, and
    wherein the preceding heat drawing and the elevated-heat drawing are performed successively.

7. The tungsten wire according to claim 6, wherein
    a tensile strength of the tungsten wire is at least 4800 MPa.

8. The tungsten wire according to claim 6, wherein
    a tungsten content of the tungsten wire is at least 90 wt %.

9. A tungsten product comprising: the tungsten wire according to claim 6.

10. The tungsten product according to claim 9, wherein
    the tungsten product is a saw wire, a twisted wire, a rope, or a medical device component.

11. The tungsten wire according to claim 6, wherein
    the temperature at which the elevated-heat drawing is performed is greater than a temperature at which the final drawing is performed, and
    wherein the temperature at which the final drawing is performed is room temperature.

* * * * *